(12) United States Patent
Morita et al.

(10) Patent No.: US 10,126,239 B2
(45) Date of Patent: Nov. 13, 2018

(54) OPTICAL WAVEGUIDE, AND SPR SENSOR CELL AND COLORIMETRIC SENSOR CELL EACH USING SAME

(71) Applicant: NITTO DENKO CORPORATION, Ibaraki-shi, Osaka (JP)

(72) Inventors: Shigenori Morita, Ibaraki (JP); Tomohiro Kontani, Ibaraki (JP); Mayu Ozaki, Ibaraki (JP); Chiharu Odane, Ibaraki (JP); Kazutaka Hara, Ibaraki (JP); Manabu Miyazaki, Ibaraki (JP)

(73) Assignee: NITTO DENKO CORPORATION, Ibaraki-shi, Osaka (JP)

( * ) Notice: Subject to any disclaimer, the term of this patent is extended or adjusted under 35 U.S.C. 154(b) by 112 days.

(21) Appl. No.: 15/030,849

(22) PCT Filed: Sep. 1, 2014

(86) PCT No.: PCT/JP2014/072888
§ 371 (c)(1),
(2) Date: Apr. 20, 2016

(87) PCT Pub. No.: WO2015/060017
PCT Pub. Date: Apr. 30, 2015

(65) Prior Publication Data
US 2016/0258864 A1 Sep. 8, 2016

(30) Foreign Application Priority Data
Oct. 21, 2013 (JP) .................................. 2013-218114

(51) Int. Cl.
*G01J 1/04* (2006.01)
*G01N 21/552* (2014.01)
(Continued)

(52) U.S. Cl.
CPC ......... *G01N 21/553* (2013.01); *G01N 21/251* (2013.01); *G01N 21/7703* (2013.01);
(Continued)

(58) Field of Classification Search
CPC ............... G01N 21/553; G01N 21/251; G01N 21/7703; G01N 21/552; G01N 2021/258; G01N 2201/08; G02B 6/1226
See application file for complete search history.

(56) References Cited

U.S. PATENT DOCUMENTS

| 4,321,057 A | 3/1982 | Buckles |
| 4,399,099 A | 8/1983 | Buckles |

(Continued)

FOREIGN PATENT DOCUMENTS

| JP | H08226894 A | 9/1996 |
| JP | 2000019100 A | 1/2000 |

(Continued)

OTHER PUBLICATIONS

ISA Japanese Patent Office, International Search Report Issued in Application No. PCT/JP2014/072888, dated Oct. 28, 2014, WIPO, 4 pages.

*Primary Examiner* — Thanh Luu
(74) *Attorney, Agent, or Firm* — Alleman Hall Creasman & Tuttle LLP

(57) ABSTRACT

The present invention provides a sensor cell that has excellent measurement accuracy in repetitive measurement. An optical waveguide of the present invention includes a cladding layer and a core layer buried in the cladding layer so that at least one surface of the core layer is exposed. A water contact angle of a surface of the cladding layer on which the core layer is exposed is 80° or more. An SPR sensor cell and a colorimetric sensor cell of the present invention each include the optical waveguide of the present invention.

5 Claims, 6 Drawing Sheets

(51) Int. Cl.
  *G01N 21/77*  (2006.01)
  *G01N 21/25*  (2006.01)
(52) U.S. Cl.
  CPC ..... *G01N 21/552* (2013.01); *G01N 2021/258* (2013.01); *G01N 2201/08* (2013.01)

(56) References Cited

U.S. PATENT DOCUMENTS

| | | |
|---|---|---|
| 6,432,364 B1 | 8/2002 | Negami et al. |
| 6,507,402 B2 | 1/2003 | Negami et al. |
| 7,682,567 B2 | 3/2010 | Itsuji et al. |
| 2002/0005953 A1 | 1/2002 | Negami et al. |
| 2005/0136685 A1* | 6/2005 | Takenaka .......... B01L 3/502723 438/778 |
| 2007/0148047 A1 | 6/2007 | Itsuji et al. |
| 2011/0014432 A1 | 1/2011 | Terada |
| 2013/0259418 A1 | 10/2013 | Kontani |

FOREIGN PATENT DOCUMENTS

| | | |
|---|---|---|
| JP | 2002022654 A | 1/2002 |
| JP | 2006153852 A | 6/2006 |
| JP | 2009226613 A | 10/2009 |
| JP | 2010019320 A | 1/2010 |
| JP | 2010112896 A | 5/2010 |
| JP | 2012107901 A | 6/2012 |
| JP | 2012122915 A | 6/2012 |
| JP | 2012215541 A | 11/2012 |

\* cited by examiner

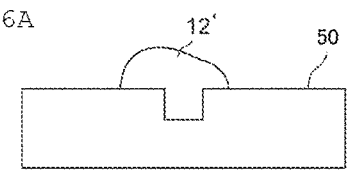
FIG. 6A
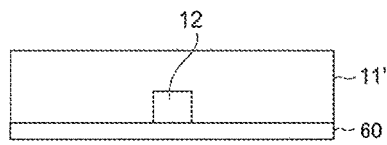
FIG. 6E
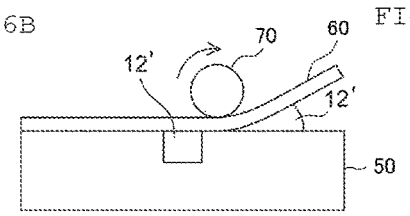
FIG. 6B
FIG. 6F
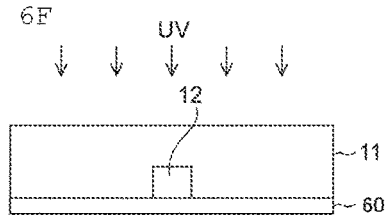
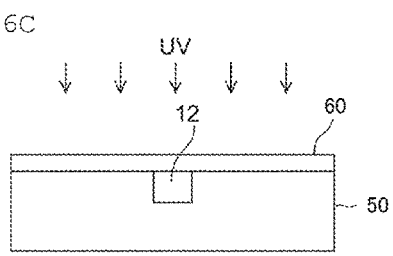
FIG. 6C
FIG. 6G
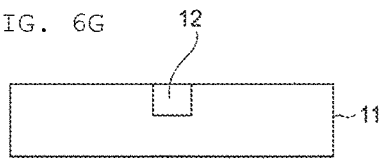
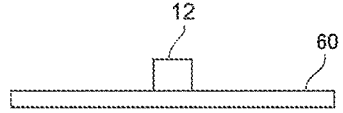
FIG. 6D

OPTICAL WAVEGUIDE, AND SPR SENSOR CELL AND COLORIMETRIC SENSOR CELL EACH USING SAME

TECHNICAL FIELD

The present invention relates to an optical waveguide, and a surface plasmon resonance (SPR) sensor cell and a colorimetric sensor cell each using the optical waveguide.

BACKGROUND ART

In recent years, an SPR sensor cell in which an optical waveguide is used as a detection unit (Patent Literature 1) has been proposed. In general, the optical waveguide includes a core layer and a cladding layer, and forms the detection unit together with a metal layer for covering an upper surface of the core layer. When a liquid sample is repeatedly placed on such a detection unit to be measured, measurement values thereof may be varied.

CITATION LIST

Patent Literature

PTL 1: JP 2000-19100 A

SUMMARY OF INVENTION

Technical Problem

The present invention provides a sensor cell that has excellent measurement accuracy in repetitive measurement.

Solution to Problem

According to one embodiment of the present invention, there is provided an optical waveguide, including a cladding layer and a core layer buried in the cladding layer so that at least one surface of the core layer is exposed, in which a water contact angle of a surface of the cladding layer on which the core layer is exposed is 80° or more.

In one embodiment of the present invention, the cladding layer includes a resin for forming a cladding layer and particles dispersed in the resin for forming a cladding layer.

In one embodiment of the present invention, a filling ratio of the particles in the cladding layer is from 2% to 75%.

In one embodiment of the present invention, an average particle diameter ($\varphi$) of the particles is from 200 nm to 2.5 µm.

According to another aspect of the present invention, there is provided an SPR sensor cell. The SPR sensor cell includes the optical waveguide.

According to yet another aspect of the present invention, there is provided a colorimetric sensor cell. The colorimetric sensor cell includes the optical waveguide.

Advantageous Effects of Invention

According to the one embodiment of the present invention, a sensor cell having excellent measurement accuracy in repetitive measurement, and an optical waveguide to be suitably used in the sensor cell are provided.

BRIEF DESCRIPTION OF DRAWINGS

FIGS. 6A to 6G are schematic views for illustrating an example of a method of manufacturing the optical waveguide of the present invention.

DESCRIPTION OF EMBODIMENTS

[A. Optical Waveguide]

An optical waveguide of the present invention includes a cladding layer having a predetermined water contact angle, and a core layer buried in the cladding layer so that at least one surface of the core layer is exposed. An optical loss (propagation loss) of the optical waveguide of the present invention at a wavelength of 660 nm is, for example, less than 2.6 dB/cm, preferably 2.0 dB/cm or less, more preferably 1.5 dB/cm or less. When the optical loss falls within this range, the optical waveguide can be used as a detection unit of a sensor cell such as an SPR sensor cell or a colorimetric sensor cell that are described later. The optical loss is measured by using a cutback technique.

Figure 1:
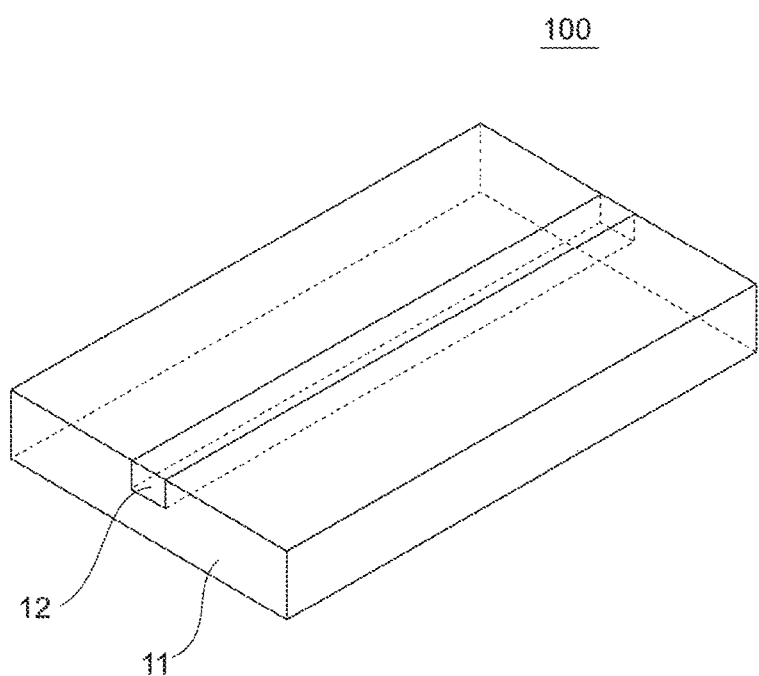
FIG. 1 is a schematic perspective view for illustrating an optical waveguide according to a preferred embodiment of the present invention.

FIG. 1 is a schematic perspective view for illustrating an optical waveguide according to a preferred embodiment of the present invention. In the illustrated example, an optical waveguide 100 includes a cladding layer 11 and a core layer 12 buried in the cladding layer 11 so that an upper surface of the core layer 12 is exposed. The optical waveguide 100 is formed into a flat plate-like shape having a substantially rectangular shape in a plan view. The thickness of the cladding layer (thickness from the upper surface of the core layer) is, for example, from 5 µm to 400 µm. It should be noted that, unlike the illustrated example, the upper surface and a lower surface of the core layer may be exposed from the cladding layer.

The cladding layer 11 preferably includes a resin for forming a cladding layer and particles dispersed in the resin for forming a cladding layer. Due to the particles dispersed in the cladding layer, the cladding layer can have a rough surface.

Any suitable particles can be used as the particles. For example, the particles are made of a material having a refractive index of preferably from 1.40 to 3.00, more preferably from 1.43 to 2.60. Using such a material has an advantage in that a refractive index of the cladding layer is easily adjusted to fall within a desired range. Further, for example, the particles are made of a material having an extinction coefficient of preferably 0.1 or less, more preferably 0. It should be noted that the refractive index as used herein means a refractive index at a wavelength of 830 nm. Further, the extinction coefficient as used herein means an extinction coefficient at the wavelength of 830 nm.

A metal and an inorganic oxide are given as specific examples of a material for forming the particles. Preferred examples of the metal may include titanium, tantalum, aluminum, zinc, chromium, and iron. In addition, preferred examples of the inorganic oxide may include metal oxides (such as titanium oxide ($TiO_2$), tantalum oxide ($Ta_2O_5$), aluminum oxide ($Al_2O_3$), zinc oxide (ZnO), chromium oxide ($Cr_2O_3$), iron oxide ($Fe_2O_3$), and copper oxide (CuO))

and metalloid oxides (such as boron oxide ($B_2O_3$), silicon oxide ($SiO_2$), and germanium oxide ($GeO_2$)). The particles may be used alone or in combination.

An average particle diameter (φ) of the particles is, for example, from 10 nm to 5 μm. The lower limit of the average particle diameter is preferably 200 nm, more preferably 300 nm. Further, the upper limit of the average particle diameter is preferably 2.5 μm, more preferably 2.0 μm. With such an average particle diameter, the water contact angle of the surface of the cladding layer can be set to fall within a desired range while suppressing the optical loss. It should be noted that the average particle diameter as used herein means a median diameter. The average particle diameter of the particles in the cladding layer can be obtained based on, for example, laser diffraction/scattering particle size distribution measurement, or a volume-based particle size distribution that is obtained from a particle size distribution determined through image processing of an scanning electron microscope (SEM) image of a cross section of the cladding layer.

Any suitable resin capable of forming the cladding layer having a lower refractive index than the core layer described later may be used as the resin for forming a cladding layer. Specific examples thereof include a fluorine resin, an epoxy resin, a polyimide resin, a polyamide resin, a silicone resin, an acrylic resin, and modified products thereof (for example, a fluorene-modified product, a deuterium-modified product, and a fluorine-modified product in the case of the resins other than the fluorine resin). Those resins may be used alone or in combination. Those resins can each be used as a photosensitive material preferably by being blended with a photosensitizing agent.

A refractive index of the resin for forming a cladding layer is lower than the refractive index of the particles. A difference between the refractive index of the resin for forming a cladding layer and the refractive index of the particles is preferably 0.03 or more, more preferably 0.05 or more, still more preferably 0.07 or more, even still more preferably 0.10 or more.

The refractive index of the resin for forming a cladding layer is preferably 1.42 or less, more preferably less than 1.40, still more preferably 1.38 or less.

A filling ratio of the particles in the cladding layer 11 is, for example, from 1% to 75%. The lower limit of the filling ratio is preferably 2%, more preferably 3%, still more preferably 5%. Further, the upper limit of the filling ratio is preferably 50%, more preferably 30%, still more preferably 25%. With such a filling ratio, the water contact angle of the surface of the cladding layer can be set to fall within a desired range while suppressing the optical loss.

A refractive index ($N_{CL}$) of the cladding layer 11 is lower than a refractive index ($N_{PA}$) of the particles. A difference ($N_{PA}-N_{CL}$) between the refractive index of the cladding layer and the refractive index of the particles is preferably 0.03 or more, more preferably 0.05 or more, still more preferably 0.07 or more, even still more preferably 0.10 or more.

The water contact angle of the surface of the cladding layer 11 on which the core layer is exposed is, for example, 80° or more, preferably 85° or more and less than 110°, more preferably 90° or more and less than 110°, still more preferably 95° or more and less than 110°. When the optical waveguide having the water contact angle of 80° or more is used as the detection unit of the sensor cell, accuracy of repetitive measurement can be improved. Meanwhile, when the water contact angle is 110° or more, the optical loss due to unevenness on an interface between the core layer and the cladding layer is increased, and the effect may not be obtained sufficiently. The value of the water contact angle is measured in accordance with Japanese Industrial Standard (JIS) R3257.

The core layer 12 is formed substantially in a square column shape extending in a direction orthogonal to both a width direction and a thickness direction of the cladding layer 11, and is buried in an upper end portion substantially at the center of the width direction of the cladding layer 11. The direction in which the core layer 12 extends serves as a direction in which light is propagated in the optical waveguide.

The core layer 12 is arranged so that the upper surface thereof is flush with an upper surface of the cladding layer 11. The metal layer can be arranged efficiently only on an upper side of the core layer in the SPR sensor cell, which is described later, by arranging the core layer so that the upper surface thereof is flush with the upper surface of the cladding layer. Further, the core layer is arranged so that both end surfaces thereof in the extending direction are flush with both end surfaces of the cladding layer in the extending direction.

A refractive index ($N_{CO}$) of the core layer 12 can be set to any suitable value depending on intended use and the like. For example, when the optical waveguide 100 is applied to an SPR sensor cell, the refractive index ($N_{CO}$) of the core layer 12 is preferably 1.43 or less, more preferably less than 1.40, still more preferably 1.38 or less. When the refractive index of the core layer is set to 1.43 or less, the detection sensitivity can be markedly improved. The lower limit of the refractive index of the core layer is preferably 1.34. When the refractive index of the core layer is 1.34 or more, SPR can be excited even in an aqueous solution-based sample (refractive index of water: 1.33), and a generally used material can be used.

The refractive index ($N_{CO}$) of the core layer 12 is higher than the refractive index ($N_{CL}$) of the cladding layer 11. The difference ($N_{CO}-N_{CL}$) between the refractive index of the core layer and the refractive index of the cladding layer is preferably 0.010 or more, more preferably 0.020 or more, still more preferably 0.025 or more. When the difference between the refractive index of the core layer and the refractive index of the cladding layer falls within such range, the optical waveguide 100 can be set to a so-called multimode. Thus, the amount of light transmitted through the optical waveguide can be increased, and the S/N ratio can be enhanced when the optical waveguide is applied to the SPR sensor cell or the colorimetric sensor cell that are described later. Further, the difference between the refractive index of the core layer and the refractive index of the cladding layer is preferably 0.15 or less, more preferably 0.10 or less, still more preferably 0.050 or less.

The thickness of the core layer 12 is, for example, from 5 μm to 200 μm, preferably from 20 μm to 200 μm. Further, the width of the core layer is, for example, from 5 μm to 200 μm, preferably from 20 μm to 200 μm. When the core layer has such thickness and/or width, the optical waveguide 100 can be set to the so-called multimode. Further, the length (waveguide length) of the core layer 12 is, for example, from 2 mm to 50 mm, preferably from 10 mm to 20 mm.

As a material for forming the core layer 12, any suitable material can be used as long as the effects of the present invention can be obtained. For example, the core layer 12 may be formed of a resin that is similar to the resin for forming a cladding layer and is adjusted so as to have a higher refractive index than the cladding layer.

It should be noted that one core layer is illustrated in FIG. 1, but the number of the core layers may be changed depending on the objective. Specifically, a plurality of core layers may be formed in a width direction of the cladding layer at predetermined intervals. Further, as the shape of the core layer, any suitable shape (for example, a semi-cylindrical shape or a convex cylindrical shape) may be employed depending on purposes.

[B. SPR Sensor Cell]

Figure 2:
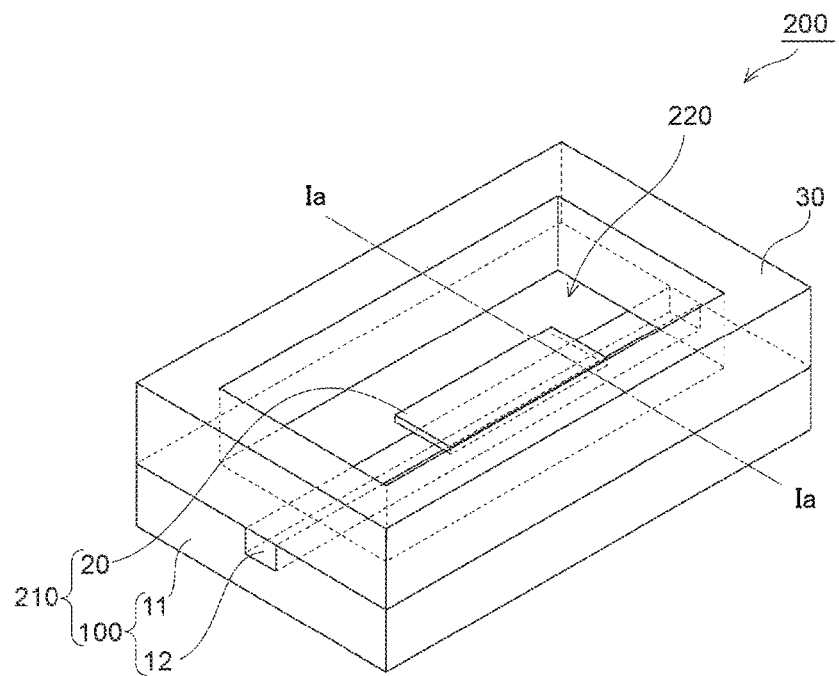
FIG. 2 is a schematic perspective view of an SPR sensor cell according to the preferred embodiment of the present invention.
Figure 3:
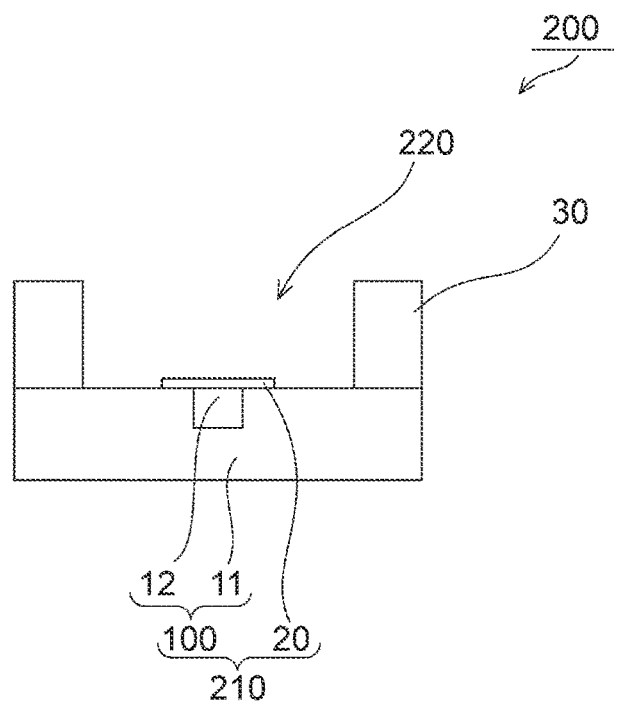
FIG. 3 is a schematic sectional view of the SPR sensor cell illustrated in FIG. 2 taken along the line Ia-Ia.

FIG. 2 is a schematic perspective view of an SPR sensor cell according to the preferred embodiment of the present invention. FIG. 3 is a schematic sectional view of the SPR sensor cell illustrated in FIG. 2 taken along the line Ia-Ia.

An SPR sensor cell 200 has, as illustrated in FIG. 2 and FIG. 3, a bottomed frame shape having a substantially rectangular shape in a plan view, and includes the optical waveguide 100 including the under-cladding layer 11 and the core layer 12 buried in the under-cladding layer 11 so that the upper surface of the core layer 12 is exposed, and a metal layer 20 for covering the under-cladding layer 11 and the core layer 12. The optical waveguide 100 and the metal layer 20 serve as a detection unit 210 configured to detect a state of a sample and/or a change thereof. In the illustrated embodiment, the SPR sensor cell 200 includes a sample placing portion 220 formed so as to be adjacent to the detection unit 210. The sample placing portion 220 is defined by an over-cladding layer 30. The over-cladding layer 30 may be omitted as long as the sample placing portion 220 can be formed appropriately. In the sample placing portion 220, a sample (for example, a solution or powder) to be analyzed is placed so as to come into contact with the detection unit (substantially, the metal layer).

The optical waveguide 100 is as described in the Section A above.

As illustrated in FIG. 2 and FIG. 3, the metal layer 20 is formed so as to uniformly cover at least a part of the upper surfaces of the under-cladding layer 11 and the core layer 12. An easy-adhesion layer (not shown) may be formed between the under-cladding layer and the metal layer and between the core layer and the metal layer as necessary. By forming the easy-adhesion layer, the metal layer can be fixed to the under-cladding layer and the core layer firmly.

As a material for forming the metal layer, there may be given gold, silver, platinum, copper, aluminum, and alloys thereof. The metal layer may be a single layer or may have a laminate structure of two or more layers. The thickness (total thickness of all the layers in the case of the laminate structure) of the metal layer is preferably from 20 nm to 70 nm, more preferably from 30 nm to 60 nm.

As a material for forming the easy-adhesion layer, there may be typically given chromium or titanium. The thickness of the easy-adhesion layer is preferably from 1 nm to 5 nm.

As illustrated in FIG. 2, the over-cladding layer 30 is formed into the shape of a frame having a rectangular shape in a plan view so that an outer periphery of the over-cladding layer 30 becomes substantially flush with an outer periphery of the optical waveguide 100 in a plan view, on the upper surface of the optical waveguide 100. A portion surrounded by the upper surfaces of the optical waveguide 100 and the over-cladding layer 30 is partitioned as the sample placing portion 220. By placing a sample in the partitioned portion, the metal layer of the detection unit 210 and the sample come into contact with each other so that detection can be performed. Further, by forming such partitioned portion, a sample can be easily placed on the surface of the metal layer, and hence the operability can be enhanced.

As a material for forming the over-cladding layer 30, for example, there may be given the materials for forming the core layer and the under-cladding layer, and silicone rubber. The thickness of the over-cladding layer is preferably from 5 µm to 2,000 µm, more preferably from 25 µm to 200 µm. The refractive index of the over-cladding layer is preferably lower than the refractive index of the core layer. In one embodiment, the refractive index of the over-cladding layer is equal to the refractive index of the under-cladding layer.

Although the SPR sensor cell according to the preferred embodiment of the present invention has been described above, the present invention is not limited thereto. For example, a lid may be provided on an upper portion of the SPR sensor cell 200 (sample placing portion 220). With such a configuration, a sample can be prevented from coming into contact with ambient air. In addition, in the case where the sample is a solution, a change in concentration caused by evaporation of a solvent can be prevented. In the case of providing a lid, an injection port for injecting a liquid sample into the sample mounting portion and a discharge port for discharging the liquid sample from the sample mounting portion may be formed. With such a configuration, the sample can be allowed to flow to be supplied to the sample mounting portion continuously, and hence the characteristics of the sample can be measured continuously.

An example of the manner of use of such an SPR sensor 200 is described below.

First, a sample is mounted on the sample mounting portion 220 of the SPR sensor cell 200 so that the sample and the metal layer 20 are brought into contact with each other. Then, light from any suitable light source is guided to the SPR sensor cell 200 (core layer 12). The light guided to the SPR sensor cell 200 (core layer 12) is transmitted through the SPR sensor cell 200 (core layer 12) while repeating total reflection in the core layer 12, and part of the light enters the metal layer 20 on an upper surface of the core layer 12 and is attenuated by surface plasmon resonance. The light transmitted through and output from the SPR sensor cell 200 (core layer 12) is guided to any suitable optical measuring instrument. That is, the intensity of light having a wavelength generating surface plasmon resonance in the core layer 12 is attenuated in the light guided from the SPR sensor 200 to the optical measuring instrument. The wavelength of light generating surface plasmon resonance depends on, for example, the refractive index of the sample brought into contact with the metal layer 20. Therefore, through the detection of the attenuation of the light intensity of the light guided to the optical measuring instrument, a refractive index of the sample or a change of the refractive index can be detected.

[C. Colorimetric Sensor Cell]

Figure 4:
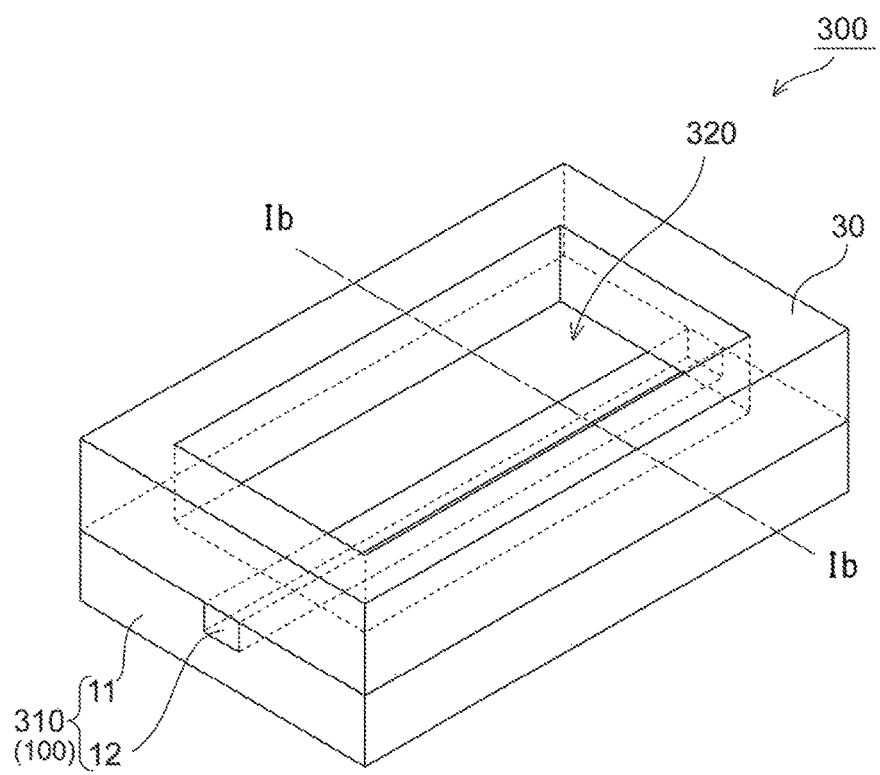
FIG. 4 is a schematic perspective view of a colorimetric sensor cell according to the preferred embodiment of the present invention.
Figure 5:
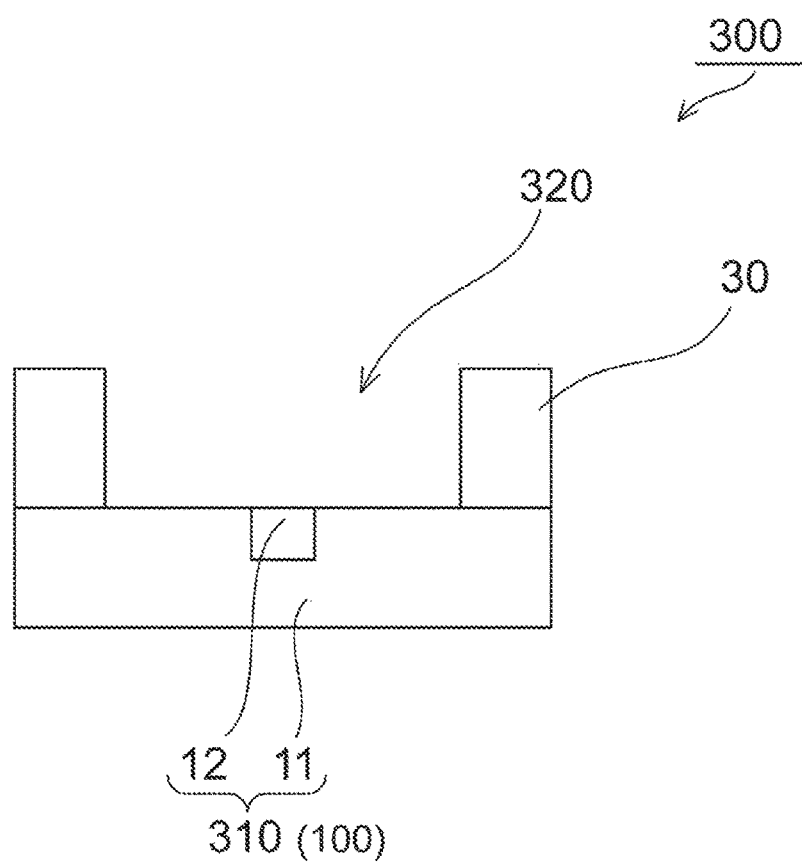
FIG. 5 is a schematic sectional view of the colorimetric sensor cell illustrated in FIG. 4 taken along the line Ib-Ib.

FIG. 4 is a schematic perspective view for illustrating a colorimetric sensor cell according to the preferred embodiment of the present invention. FIG. 5 is a schematic sectional view of the colorimetric sensor cell illustrated in FIG. 4 taken along the line Ib-Ib.

The calorimetric sensor cell 300 has, as illustrated in FIG. 4 and FIG. 5, a bottomed frame shape having a substantially rectangular shape in a plan view, and includes the optical waveguide 100 including the under-cladding layer 11 and the core layer 12 buried in the under-cladding layer 11 so that the upper surface of the core layer 12 is exposed. The optical waveguide 100 serves as a detection unit 310 configured to detect a state of a sample and/or a change thereof. In the illustrated embodiment, the colorimetric sensor cell 300 further includes a sample placing portion 320 formed so as to be adjacent to the detection unit 310 (optical waveguide 100). The sample placing portion 320 is defined by the over-cladding layer 30. The over-cladding layer 30 may be omitted as long as the sample placing portion 320 can be formed appropriately. In the sample placing portion 320, a sample (for example, a solution or powder) to be analyzed is placed so as to come into contact with the detection unit. Further, although not illustrated, similarly to the SPR sensor cell described in the Section B above, a lid may be provided on the colorimetric sensor cell 300 (sample placing portion 320).

The optical waveguide 100 is as illustrated in the Section A above. Further, the over-cladding layer 30 is as illustrated in the Section B above.

An example of the manner of use of such a colorimetric sensor cell 300 is described below.

First, a sample is placed on the sample placing portion 320 of the colorimetric sensor cell 300 so that the sample and the detection unit 310 (optical waveguide 100) are brought into contact with each other. Then, light from any suitable light source is guided to the colorimetric sensor cell 300 (core layer 12). The light guided to the colorimetric sensor cell 300 (core layer 12) transmits through the colorimetric sensor cell 300 (core layer 12), while repeating total reflection in the core layer 12. Part of the light leaks out of the core layer 12 as an evanescent wave, and enters the sample on the upper surface of the core layer 12 to be attenuated. The light that has transmitted through the colorimetric sensor cell 300 (core layer 12) to be emitted is guided to any suitable light measuring instrument. That is, the intensity of light having a wavelength that is absorbed by the sample on the core layer 12 is attenuated in the light guided from the colorimetric sensor cell 300 to the light measuring instrument. The wavelength that is absorbed by the sample differs depending on, for example, a color of the sample placed on the colorimetric sensor cell 300, and hence the color of the sample and a change thereof can be detected through detection of the attenuation of the light intensity of the light guided to the light measuring instrument.

[D. Manufacturing Method]

As a method of manufacturing the optical waveguide of the present invention, any suitable method can be used. As a specific example of the method of producing the optical waveguide of the present invention, a method illustrated in FIGS. 6A to 6G or a method illustrated in FIG. 3 of JP2012-215541A is given.

In the method illustrated in FIGS. 6A to 6G, first, as illustrated in FIG. 6A, a material 12' for forming a core layer is applied on a surface of a die 50 having a recessed portion corresponding to the shape of the core layer. Then, as illustrated in FIG. 6B, a transfer film 60 is bonded onto the surface of the die 50 while the transfer film 60 is pressed in a predetermined direction with pressing means 70 so that the excessive material 12' for forming a core layer is removed while the material 12' for forming a core layer is filled into the recessed portion. After that, as illustrated in FIG. 6C, the material 12' for forming a core layer filled into the recessed portion is irradiated with ultraviolet rays to cure the material, to thereby form the core layer 12. In addition, as illustrated in FIG. 6D, the transfer film 60 is peeled from the die 50, and the core layer 12 is thus transferred onto the transfer film 60.

Then, as illustrated in FIG. 6E, a material 11' for forming a cladding layer, which includes a resin for forming a cladding layer and particles dispersed in the resin as appropriate, is applied on the transfer film 60 so as to cover the core layer 12. Alternatively, unlike the illustrated example, the material 11' for forming a cladding layer may be applied on another support (for example, a polyethelene terephthalate (PET) film subjected to corona treatment) in advance, and the support and the transfer film 60 may be bonded to each other so that the material 11' for forming a cladding layer covers the core layer 12. After that, as illustrated in FIG. 6F, the material 11' for forming a cladding layer is irradiated with ultraviolet rays to cure the material, to thereby form the cladding layer 11. Then, as illustrated in FIG. 6G, the transfer film 60 is removed by peeling and the resultant is flipped upside down, to thereby obtain the optical waveguide including the core layer 12 buried in the cladding layer 11.

The irradiation conditions for the ultraviolet rays can be appropriately set depending on the kinds of the materials. The materials may be heated as needed. The heating may be performed before the ultraviolet ray irradiation, after the ultraviolet ray irradiation, or simultaneously with the ultraviolet ray irradiation. Further, as a method of dispersing the particles in the resin for forming a cladding layer, any suitable method can be used.

The SPR sensor cell and the colorimetric sensor cell of the present invention can be obtained by forming desired components (a metal layer, an over-cladding layer, and the like) on the core exposed surface of the optical waveguide of the present invention. As methods of forming those components, methods described in JP2012-107901A, JP2012-215541A, and the like can be used.

EXAMPLES

The present invention is hereinafter described specifically by way of Examples. However, the present invention is not limited to the Examples below.

<Refractive Index>

The refractive index was measured by forming a film having a thickness of 10 μm on a silicon wafer and measuring the refractive index of the film at a wavelength of 830 nm through use of a prism coupler refractive index measurement device.

<Filling Ratio>

The filling ratio of the particles was calculated based on the following expression.

Filling ratio (%)=((particle mixing rate (wt %)/bulk specific gravity (g/ml))/(100+particle mixing rate (wt %)))×100

<Bulk Specific Gravity>

The bulk specific gravity of the particles was calculated by putting the particles into a cup having a known volume (mL), measuring a particle weight (g), and dividing the particle weight by the cup volume.

<Average Particle Diameter>

A median diameter calculated through the laser diffraction/scattering particle size distribution measurement was used as the average particle diameter.

<Water Contact Angle>

In accordance with JIS R3257, the water contact angle of the upper surface of the cladding layer (core layer exposed surface) was measured by using an automatic contact angle meter ("Drop Master 500" (model number) manufactured by Kyowa Interface Science Co., LTD.).

Example 1

An optical waveguide film was produced by a method illustrated in FIGS. 6A to 6G. Specifically, a material for forming a core layer was dropped onto a surface of a die (length: 200 mm, width: 200 mm) in which a recessed portion for forming a core layer having a width of 50 μm and a length (depth) of 50 μm was formed on the surface of the die. One end of a corona-treated surface of a polypropylene (PP) film (thickness: 40 μm) having one surface subjected to corona treatment was brought into abutment against the surface of the die, and the other end was allowed to be warped. In this state, a roller was rotated toward the other end side while pressing the abutment part between the die and the PP film from the PP film side, to thereby bond the die and the PP film to each other. With this, the material for forming a core layer was filled into the recessed portion of the die, and thus the excessive material for forming a core layer was pushed out. Then, the laminate thus obtained was irradiated with ultraviolet rays from the PP film side to cure the material for forming a core layer completely, to thereby form a core layer (refractive index: 1.384). It should be noted that the material for forming a core layer was prepared by stirring and dissolving 60 parts by weight of a fluorine-based UV-curable resin ("OP38Z" (trade name) manufactured by DIC Corporation) and 40 parts by weight of a fluorine-based UV-curable resin ("OP40Z" (trade name) manufactured by DIC Corporation). Then, the PP film was peeled from the die to transfer the core layer having a substantially square column shape with a thickness of 50 μm and a width of 50 μm onto the film.

A material for forming a cladding layer was applied to the PP film so as to cover the core layer. It should be noted that the material for forming a cladding layer was prepared by mixing 93.5 parts by weight of a fluorine-based UV curable resin ("Fluor® link MD700" (trade name) manufactured by Solvay Specialty Polymers Japan K.K., refractive index: 1.348) and 6.5 parts by weight of silica particles ("Admafine SC1500-SMJ" (trade name) manufactured by Admatechs Company Limited, refractive index: 1.45). At this time, the material for forming a cladding layer was applied so that the thickness from a surface (upper surface) of the core layer became 100 μm. Then, the resultant was irradiated with ultraviolet rays to cure the material for forming a cladding layer, to thereby form a cladding layer. Then, the PP film was removed by peeling and the cladding layer and the core layer were inverted. As described above, an optical waveguide film having a core layer buried in a cladding layer was produced.

Example 2

An optical waveguide film was produced in the same way as in Example 1 except that the mixing rate of the silica particles in the material for forming a cladding layer was set to 10 wt %.

Example 3

An optical waveguide film was produced in the same way as in Example 1 except that different silica particles ("Admafine SC2500-SMJ" (trade name) manufactured by Admatechs Company Limited) were used, and the mixing rate of the silica particles in the material for forming a cladding layer was set to 0.6 wt %.

Example 4

An optical waveguide film was produced in the same way as in Example 1 except that different silica particles ("Admafine SC2500-SMJ" (trade name) manufactured by Admatechs Company Limited) were used, and the mixing rate of the silica particles in the material for forming a cladding layer was set to 2.5 wt %.

Example 5

An optical waveguide film was produced in the same way as in Example 1 except that different silica particles ("Admafine SC2500-SMJ" (trade name) manufactured by Admatechs Company Limited) were used, and the mixing rate of the silica particles in the material for forming a cladding layer was set to 5 wt %.

Example 6

An optical waveguide film was produced in the same way as in Example 1 except that different silica particles ("Admafine SC2500-SMJ" (trade name) manufactured by Admatechs Company Limited) were used, and the mixing rate of the silica particles in the material for forming a cladding layer was set to 10 wt %.

Example 7

An optical waveguide film was produced in the same way as in Example 1 except that different silica particles ("Admafine SC2500-SMJ" (trade name) manufactured by Admatechs Company Limited) were used, and the mixing rate of the silica particles in the material for forming a cladding layer was set to 26 wt %.

Example 8

An optical waveguide film was produced in the same way as in Example 1 except that different silica particles ("Admafine SC5500-SMJ" (trade name) manufactured by Admatechs Company Limited) were used, and the mixing rate of the silica particles in the material for forming a cladding layer was set to 0.8 wt %.

Example 9

An optical waveguide film was produced in the same way as in Example 1 except that different silica particles ("Admafine SC5500-SMJ" (trade name) manufactured by Admatechs Company Limited) were used, and the mixing rate of the silica particles in the material for forming a cladding layer was set to 2 wt %.

Example 10

An optical waveguide film was produced in the same way as in Example 1 except that different silica particles ("Admafine SC5500-SMJ" (trade name) manufactured by Admatechs Company Limited) were used, and the mixing rate of the silica particles in the material for forming a cladding layer was set to 5 wt %.

Example 11

An optical waveguide film was produced in the same way as in Example 1 except that different silica particles ("Admafine SC5500-SMJ" (trade name) manufactured by Admatechs Company Limited) were used, and the mixing rate of the silica particles in the material for forming a cladding layer was set to 10 wt %.

Example 12

An optical waveguide film was produced in the same way as in Example 1 except that different silica particles ("AEROSIL R974" (trade name) manufactured by Nippon Aerosil Co., Ltd., refractive index: 1.45) were used, and the mixing rate of the silica particles in the material for forming a cladding layer was set to 2.6 wt %.

Example 13

An optical waveguide film was produced in the same way as in Example 1 except that different silica particles ("AEROSIL R974" (trade name) manufactured by Nippon Aerosil Co., Ltd., refractive index: 1.45) were used, and the mixing rate of the silica particles in the material for forming a cladding layer was set to 5 wt %.

Example 14

An optical waveguide film was produced in the same way as in Example 1 except that different silica particles ("SYLOPHOBIC 507" (trade name) manufactured by Fuji Silysia Chemical Ltd., refractive index: 1.45) were used, and the mixing rate of the silica particles in the material for forming a cladding layer was set to 3.2 wt %.

Example 15

An optical waveguide film was produced in the same way as in Example 1 except that different silica particles ("SYLOPHOBIC 702" (trade name) manufactured by Fuji Silysia Chemical Ltd., refractive index: 1.45) were used, and the mixing rate of the silica particles in the material for forming a cladding layer was set to 4 wt %.

Example 16

An optical waveguide film was produced in the same way as in Example 1 except that different silica particles ("SYLOPHOBIC 702" (trade name) manufactured by Fuji Silysia Chemical Ltd., refractive index: 1.45) were used, and the mixing rate of the silica particles in the material for forming a cladding layer was set to 7.2 wt %.

Example 17

An optical waveguide film was produced in the same way as in Example 1 except that different silica particles ("SYLOPHOBIC 702" (trade name) manufactured by Fuji Silysia Chemical Ltd., refractive index: 1.45) were used, and the mixing rate of the silica particles in the material for forming a cladding layer was set to 25 wt %.

Example 18

An optical waveguide film was produced in the same way as in Example 1 except that titania particles ("SRD 02-W" (trade name) manufactured by Sakai Chemical Industry Co. Ltd., crystal phase: rutile type, refractive index: 2.72) were used, and the mixing rate of the titania particles in the material for forming a cladding layer was set to 2 wt %.

Comparative Example 1

An optical waveguide film was produced in the same way as in Example 1 except that the mixing rate of the silica particles in the material for forming a cladding layer was set to 0 wt % (that is, the silica particles were not used).

Comparative Example 2

An optical waveguide film was produced in the same way as in Example 1 except that different silica particles ("Admafine SC2500-SMJ" (trade name) manufactured by Admatechs Company Limited) were used, and the mixing rate of the silica particles in the material for forming a cladding layer was set to 0.3 wt %.

<Evaluation of Variation in Measurement Value>

Each of the optical waveguide films obtained in Examples and Comparative Examples described above was cut by dicing to a length of 22.25 mm and a width of 20 mm. Then, chromium and gold were sputtered on the core layer exposed surface in the stated order through a mask having an opening with a length of 6 mm and a width of 1 mm, to thereby form an easy-adhesion layer (thickness: 1 nm) and a metal layer (thickness: 50 nm) in the stated order so as to cover the core layer. Finally, with a method similar to the method of forming the under-cladding layer, an over-cladding layer having a frame shape was formed by using the fluorine-based UV curable resin ("FluorolinkMD700" (trade name) manufactured by Solvay Specialty Polymers Japan K.K.). In this manner, an SPR sensor cell similar to the SPR sensor cell illustrated in FIG. 2 and FIG. 3 was produced. It should be noted that a horizontal cross sectional area of a sample placing portion defined by the over-cladding layer was 24 mm$^2$ (8 mm×3 mm).

As a sample, 1 µl, of 10% ethylene glycol aqueous solution was placed on the sample placing portion of the SPR sensor cell obtained as described above, and white light from a halogen light source ("HL-2000-HP" (trade name) manufactured by Ocean Optics, Inc., white light) was caused to enter one of end portions of the core layer through a multi-mode optical fiber (φ50 µm). Further, a power meter was connected to the other one of the end portions of the core layer through a multi-mode optical fiber (φ50 µm) to thereby measure the intensity of emitted light (µW).

The measurement was repeated 10 times while a sample to be placed on the sample placing portion was changed to a new sample (10% ethylene glycol aqueous solution) for each measurement. A difference between the maximum value and the minimum value of the obtained light intensities was regarded as measurement variation. The evaluation results are shown in Table 1 together with the various characteristics of the optical waveguides.

TABLE 1

| | Average particle diameter (µm) | Mixing rate (wt %) | Filling ratio (%) | Water contact angle (°) | Variation in measurement (µW) |
|---|---|---|---|---|---|
| Example 1 | 0.3 | 6.5 | 14 | 100 | 2 |
| Example 2 | 0.3 | 10 | 30 | 105 | 2 |
| Example 3 | 0.5 | 0.6 | 2 | 90 | 5 |
| Example 4 | 0.5 | 2.5 | 8 | 95 | 4 |
| Example 5 | 0.5 | 5 | 14 | 99 | 3 |
| Example 6 | 0.5 | 10 | 25 | 102 | 2 |
| Example 7 | 0.5 | 26 | 60 | 110 | 12 |
| Example 8 | 1.9 | 0.8 | 2 | 100 | 2 |
| Example 9 | 1.9 | 2 | 5 | 104 | 2 |
| Example 10 | 1.9 | 5 | 11 | 104 | 2 |
| Example 11 | 1.9 | 10 | 20 | 105 | 2 |
| Example 12 | 0.012 | 2.6 | 34 | 85 | 6 |
| Example 13 | 0.012 | 5 | 50 | 90 | 5 |
| Example 14 | 2.7 | 3.2 | 8 | 103 | 2 |
| Example 15 | 4.1 | 4 | 12 | 105 | 2 |
| Example 16 | 4.1 | 7.2 | 20 | 105 | 2 |
| Example 17 | 4.1 | 25 | 70 | 112 | 14 |
| Example 18 | 0.035 | 2 | 30 | 90 | 5 |

TABLE 1-continued

| | Average particle diameter (μm) | Mixing rate (wt %) | Filling ratio (%) | Water contact angle (°) | Variation in measurement (μW) |
|---|---|---|---|---|---|
| Comparative Example 1 | — | — | 0 | 71 | 320 |
| Comparative Example 2 | 0.5 | 0.3 | 1 | 75 | 295 |

As is apparent from Table 1, even when the repetitive measurement is performed, the SPR sensor cells using the optical waveguides of Examples have reduced variation in emitted light intensity compared to the SPR sensor cells using the optical waveguides of Comparative Examples.

INDUSTRIAL APPLICABILITY

The optical waveguide of the present invention can be suitably used as the detection unit of the SPR sensor cell, the colorimetric sensor cell, or the like.

REFERENCE CHARACTERS LIST 11 cladding layer (under-cladding layer)
12 core layer
20 metal layer
30 over-cladding layer
100 optical waveguide
200 SPR sensor cell
300 colorimetric sensor cell

The invention claimed is:

1. An optical waveguide, comprising:
    a cladding layer comprising a resin for forming the cladding layer and particles dispersed in the resin; and
    a core layer buried in the cladding layer so that at least one surface of the core layer is exposed,
    wherein a water contact angle of a surface of the cladding layer on which the core layer is exposed is 80° or more and less than 110°.

2. The optical waveguide according to claim 1, wherein a filling ratio of the particles in the cladding layer is from 2% to 75%.

3. The optical waveguide according to claim 1, wherein an average particle diameter (φ) of the particles is from 200 nm to 2.5 μm.

4. A surface plasmon resonance (SPR) sensor cell, comprising an optical waveguide comprising:
    a cladding layer comprising a resin for forming the cladding layer and particles dispersed in the resin; and
    a core layer buried in the cladding layer so that at least one surface of the core layer is exposed,
    wherein a water contact angle of a surface of the cladding layer on which the core layer is exposed is 80° or more and less than 110°.

5. A colorimetric sensor cell, comprising an optical waveguide comprising:
    a cladding layer comprising a resin for forming the cladding layer and particles dispersed in the resin; and
    a core layer buried in the cladding layer so that at least one surface of the core layer is exposed,
    wherein a water contact angle of a surface of the cladding layer on which the core layer is exposed is 80° or more and less than 110°.

* * * * *